United States Patent [19]

Ostrea, Jr.

[11] Patent Number: 5,185,267
[45] Date of Patent: * Feb. 9, 1993

[54] METHOD FOR DETECTING MATERNALLY TRANSFERRED DRUG METABOLITES IN NEWBORN INFANTS

[75] Inventor: Enrique M. Ostrea, Jr., Farmington Hills, Mich.

[73] Assignee: The Board of Governors of Wayne State University, Detroit, Mich.

[*] Notice: The portion of the term of this patent subsequent to May 14, 2008 has been disclaimed.

[21] Appl. No.: 691,994

[22] Filed: Apr. 26, 1991

Related U.S. Application Data

[63] Continuation-in-part of Ser. No. 264,131, Oct. 28, 1988, Pat. No. 5,015,589.

[51] Int. Cl.$^5$ .............................................. G01N 33/00
[52] U.S. Cl. ...................................... 436/92; 436/161; 436/172; 436/173; 436/804; 436/816; 436/901; 435/7.1; 435/7.72; 435/7.9
[58] Field of Search ................ 435/7.1, 7.7, 7.71–7.72, 435/7.8, 7.9, 7.92–7.95; 436/92, 93, 161, 173, 172, 175, 177, 178, 800, 804, 816, 901

[56] References Cited

U.S. PATENT DOCUMENTS 5,015,589 5/1991 Ostrea, Jr. .............................. 436/92

OTHER PUBLICATIONS

Wells, D. J. et al. "Comparative results with five cannabinoid immunoassay systems at the screening threshold of 100 MUG-L", Clin Chem 35(11), pp. 2241–2243, 1989.

Clark, G. D. et al. "Analysis of cocaine and benzoylecgonine in meconium of infants born to cocaine dependant mothers", Clin Chem. 36(6), p. 1022, 1990.

Mauer, H. H. et al. "Toxicological detection of pholcodine and it's metabilites in urine and hair using radioimmunoassay, fluorescence polarization immunoassay, enzyme immunoassay and gas chromatography–mass spectrometry", Int. J. Leg. Med. 104/1, pp. 43–46, 1990.

Chan, B. et al. "Comparisor of derivatives for determination of codeine and morphine by gas chromatography/mass spectrometry", J. Anal. Toxicol., 14(1), pp. 12–17, 1990.

Maynard, E. C. et al. "Meconium for drug testing", AM. J. Dis. Child. (USA), 1991, 145/6 pp. 650–652.

Ostrea, E. M. Jr. et al. "The Detection of herion, cocaine and cannabinoid metabolites in meconium of infants drug-dependent mothers", Conference, Bethesda, Md. USA, Sep. 7–9, 1988.

Ostrea, E. M., Jr. et al. "Rapid isolation and detection of drugs in meconium of infants of drug dependent mothers", Clin Chem, 1988, 34/11 (2372-3).

1985 National Health Household Survey on Drug Abuse, Rockville. Md., 1987.

E. M. Ostrea et al., J. Pediatr. 94: 292–295, (1979).
Zelson et al., Pediatrics 48: 178 (1971).
Wilson, G. S. et al., Pediatrics 63: 135–144 (1979).
Chavez, C. J. et al., J. Pediatrics 95: 407–409 (1979).
Chasnoff, I. J. et al., Pediatrics 70: 210–213 (1982).
Chavez, C. J. et al., Pediatr. Res. 12: 367A, (1979).
Oleske, J. et al., J. Am Med. Assoc., 249: 2345–2349 (1983).
Chasnoff, I. J. et al., J. Pediatr. 108: 456–459 (1986).
Kandall, S. R., Am. J. Dis. Child, 127: 58–61 (1974).
Ostrea, E. M. et al., J. Pediatr. 88: 642–645 (1976).
Halstead, A. C. et al., Clin. Biochem. 21: 59–61 (1988).
Ostrea, E. M. et al., J. Ped. 115: 474–477 (1989).
Ostrea, E. M. et al., Clin. Chem. 34: 2372–2373 (1989).
Ostrea, E. M. et al., Dev. Pharmacol. Ther. 980; 1:163–170 (1980).
Jaffe, J., Drug addiction & drug abuse, In: Goodman, L., Gillman, A., eds. London: Collier-Macmillan, 535–584 (1989).
Ostrea E. M. et al., Pediat. Res. 27: 251A (1990).
Welch, R. A. et al., Substance Abuse (in press) (1990).

*Primary Examiner*—James C. Housel
*Assistant Examiner*—David Redding
*Attorney, Agent, or Firm*—Ian C. McLeod

[57] ABSTRACT

An improved method for detecting the presence of durg metabolites in the meconium of newborn infants is described. The method involves a single step extraction of the drug metabolites from meconium using a buffered aqueous solution containing methanol in an amount between about 10 and 30% by volume and buffered to a pH between 6 and 7 and then assaying the extract individually for the presence of the drug metabolites. The method is particularly useful for detection of cocaine, morphine, cannabinoid and amphetamine metabolites; however, any drug metabolite in the infant meconium can be tested if it is extracted by the solution from the meconium. Various assay methods are used for the drug metabolites in the solutions derived from the meconium, including immunoassays, fluorescent assays and mass spectroscopy. The method provides for early detection of drug presence in newborn infants which contribute to infant illness.

18 Claims, No Drawings

METHOD FOR DETECTING MATERNALLY TRANSFERRED DRUG METABOLITES IN NEWBORN INFANTS

CROSS-REFERENCE TO RELATED APPLICATION

This application is a continuation-in-part of application Serial No. 264,131, filed Oct. 28, 1988, now U.S. Pat. No. 5,015,589.

BACKGROUND OF THE INVENTION (1) Summary of the Invention

The present invention relates to an improved method for detecting drug metabolites which are transferred from a mother to a newborn infant during pregnancy. In particular, the method involves the isolation of meconium from a newborn infant, separation of the drug metabolites from the meconium in a single solution and assaying for the metabolites in the solution.

(2) Prior Art

The use of illicit drugs in the United States is widespread. According to a national survey in 1985, an estimated 23 million people were users of illicit drugs (1985 National Health Household Survey on Drug Abuse. Rockville, MD., 1987). Although exact figures are not known, a sizable portion of drug users are women of childbearing age or are pregnant women. Infants born to these drug dependent women have multiple problems. In the neonatal period, their mortality rate is increased as well as morbidity, which includes asphyxia, prematurity, low birth weight, hyaline membrane disease, infections, aspiration pneumonia, congenital malformations, abnormal heart rate and breathing patterns and drug withdrawal (Ostrea, E. M., Chavez, C. J., J. Pediatr. 94:292-295, (1979); Zelson, C., Rubio E., and Wasserman, E., Pediatrics 48:178 (1971)). Long term sequelae are not uncommon and include delays in physical growth and mental development, sudden infant death syndrome, hyperactivity, ocular and neurologic abnormalities and lately, a risk to acquired immunodeficiency disease (Wilson, G S., McCreary, M., Kean, J., and Baxter, J., Pediatrics 63:135-144 (1979); Chavez, C. J., et al., J. Pediatrics 95:407-409 (1979); Chasnoff, I. J., et al., Pediatrics 70:210-213 (1982); Chavez, C. J., et al., Pediatr Res 12:367A, (1979); and Oleske, J., et al., J. Am. Med. Assoc., 249:2345-2349 (1983)). At present, cocaine abuse among pregnant women has also become widespread and infant morbidity, notably cerebrovascular problems have been reported (Chasnoff, I. J., et al., J. Pediatr. 108:456-459 (1986)). Because of these immediate and long term problems, infants of drug dependent women (IDDM) constitute a high risk group and have to be identified as soon as possible after birth if intervention is to be successful.

Unfortunately, the identification of the drug exposed neonate is not easy. Many of the drugs to which the fetus is exposed, in utero, do not produce immediate or recognizable effects in the neonates (Kandall, S. R., Am. J. Dis Child, 127:58-61 (1974)). Maternal admission of drug usage is often inaccurate because of fear of the consequences stemming from such admission. Even with maternal cooperation, such information regarding the type and extent of drug usage is often inaccurate (Ostrea, E. M., et al., J. Pediatr. 88:642-645 (1976)). One alternative is to test the infant's urine for drugs, but this procedure has its limitations since successful detection of drug metabolites in the infant's urine is dependent on time of the last drug intake by the mother or when, after birth, the infant's urine was collected. A high rate of false negative results in neonatal urine tests can arise from the mother's abstention from the use of the drug a few days before she delivers or to the inability to obtain a sample of the infant's urine soon after birth (Halstead, A. C., et al., Clin. Biochem. 21:59-61 (1988)). Our experience verifies this diagnostic problem. Urine from 337 infants of known drug dependent mothers was tested by thin-layer chromatography It was found that only 13% were positive. Similarly, only 37% of the urine samples taken from drug dependent infants were positive for drugs when tested by TDX fluorescent polarization immunoassay (Ostrea, E. M., Brady, M. J., Parks, P. M., Asensio, D. C., Nalaz, A., J. Ped. 115:474-474 (1989)). Even with more sensitive methods such as radioimmunoassay, 8 urine samples tested negative for drugs despite a positive test in the stools (Ostrea, E. M., Brady, M. J., Parks, P. M., Asensio, D. C., Naluz, A., J. Ped. 115:474-474 (1989)). Clearly, there is a need for a better way to detect prenatal drug exposure in this high risk group of infants.

A new method has been developed for identifying fetal drug exposure by detecting drug metabolites in meconium, the first green stools of the newborn infant which is passed within a few days after birth (Ostrea, E. M., Parks, P., Brady, M., Clin. Chem. 34:2372-2373 (1989); Ostrea, E. M., Brady, M. J., Parks, P. M., Asensio, D. C., Naluz, A., J. Ped. 115:474-474 (1989)). The concept behind this method was based on initial research in pregnant, morphine addicted monkeys (Ostrea, E. M., Lynn, S. N., Wayne, R. H., Stryker, J. C., Dev. Pharmacol. Ther. 980; 1:163-170 (1980)) and subsequently in rats (Ostrea, E. M., Brady, M. J., Parks, P. M., Asensio, D. C., Naluz, A., J. Ped. 115:474-477 (1989)) which showed that a high concentration of drug metabolites were present in the gastrointestinal tract of their fetuses We interpreted this observation to be a consequence of the following mechanism: morphine in the fetus is metabolized by the liver to water soluble glucuronide conjugates which are then excreted into the bile or urine (Jaffe, J., Drug addiction and drug abuse. In: Goodman, L., Gillman, A., eds. *The Pharmacologic Basis of Therapeutics.* London: Collier-Macmillan, 535-584 (1989)). In either case, morphine glucuronide accumulates in the fetal intestines either from bile secretion or from fetal urine which is swallowed via the amniotic fluid Thus, meconium represents an excretion product which is cumulative of the entire gestation. Overall therefore, meconium acts as a reservoir of drug metabolites in the fetus; seemingly a stockpile of pharmacologic waste products throughout gestation.

Clinical studies have been conducted which have validated meconium analysis as a reliable drug screen in the newborn infant:

1. Meconium obtained from 20 infants of drug-dependent mothers and five control infants were analyzed by radioimmunoassay for the metabolites of heroin, cocaine and cannabinoids (Ostrea, E. M., Brady, M. J., Parks, P. M., Asensio, D. C., Naluz, A., J. Ped. 115-474-477 (1989)). Control stools showed no drug. Meconium from the infants of drug-dependent mothers showed the presence of at least one drug metabolite: 80% of the infants of drug-dependent mothers showed cocaine (range 0.14 to 19.91 $\mu$g/g stool), 55% showed morphine (range 0.41 to 14.97 $\mu$g/g stool), and 60% showed cannabinoid (range 0.05 to 0.67 $\mu$g/g stool).

The concentrations of metabolites were highest during the first 2 days; some stools tested positive up to the third day. In contrast, only 37% of the infants had positive results on a urine screen (fluorescent polarization immunoassay method).

2. Meconium testing was used to determine the prevalence of illicit drug abuse among pregnant women who delivered in a large perinatal center (Ostrea, E. M., Jr., Brady, M., Gause, S., Raymundo, A. L., Stevens M., Pediat. Res. 27:251A (1990)). A total of 3010 infants were screened for the metabolites of cocaine, morphine and cannabinoids in their meconium by radioimmunoassay: 44.3% were positive for either one of the 3 drug metabolites; 41% were positive for cocaine or morphine, 30.7% were positive for cocaine (15.4% positive for cocaine only); 20.5% positive for morphine (7.3% positive for morphine only) and 11.5% positive for cannabinoid (5.2% positive for cannabinoid only). In contrast, only 11.1% of the mothers in the entire population studied admitted to the use of drugs during pregnancy.

3. The sensitivity of meconium test is high. The method was compared to drug detection by maternal hair analysis and in depth interview of the mother (Ostrea, E. M., Martier, S., Welch, R., Brady, M. Pediatr Res. 27, 219A (1990); Welch, R. A., Martier, S. S., Ager, J. W., Ostrea, E. M., Sokol, R. J., Substance Abuse (in press) (1990)). In 26 high risk mothers studied, the abuse of one drug during pregnancy was identified by history in 19 subjects (73%); by meconium analysis in 19 subjects (73.1%) and by hair analysis in 12/16 (75%) subjects. Abuse of 2 or more drugs was identified only in 6 subjects (23%) by history, as compared to 9 subjects (34.6%) by meconium analysis and in 8 (50%) by hair analysis. There was 96% concordance of cocaine identification in hair and meconium and 73% for heroin and cannabinoids. There was also a high correlation between the cocaine concentration in meconium and in hair.

Meconium is therefore an ideal specimen for drug testing in the newborn period: (i) its collection is easy and non-invasive, (ii) it contains high concentrations of drugs and their metabolites and (ii) drugs may be present in meconium for up to the third day after birth. Meconium testing is sensitive, quantitative, and rapid. The test is therefore useful for diagnostic purposes as well as for clinical and epidemiologic research.

However, the preferred method described in U.S. Pat. application Ser. No. 264,131) is different for mass drug screening of meconium in infants since the former involve separate extractions for the different drugs with acidified water or methanol and analysis by immunoassay, particularly radio-immunoassay. It is desirable to modify the procedure to provide for mass screening and particularly to allow analysis by other methods such as enzyme immunoassay (EMIT), fluorescent polarization method, HPLC and gas chromatography/mass spectroscopy.

OBJECTS

It is therefore an object of the present invention to provide an improved method for testing for drug metabolites in infants which allows for rapid mass screening. It is further an object of the present invention to provide other methods of detection of drugs which are also reliable. Further still, it is an object of the present invention to provide an improved method which is relatively simple and economical to perform. These and other objects will become increasingly apparent by reference to the following description.

GENERAL DESCRIPTION

The present invention relates to a method for detecting maternally transferred drug metabolites in a newborn infant which comprises: isolating meconium from the newborn infant which possibly contains the transferred drug metabolites from the mother; extracting the drug metabolites from the meconium in an aqueous solution containing methanol in an amount less than about 30% by volume with a buffered pH between about 6 and 7 and assaying the solution for the drug metabolites, preferably using enzyme immunoassay (EMIT), fluorescent polarization method (TDX) and gas chromatography/mass spectroscopy. Preferably the methanol represents about 10 to 30 percent by volume of the aqueous solution The buffered aqueous methanol eliminates cross-reactivity or interference secondary to the extraction of unwanted compounds from the meconium.

The drug metabolites are preferably extracted from the meconium using a solution of 0.1 M phosphate buffered methanol (4 parts volume 0.1 M phosphate buffer [pH =6.4–6.8]and 1 part volume methanol) This mixture allows a one-step complete separation of all of the drug metabolites in meconium and the exclusion of other compounds in meconium which can cross-react in the subsequent analytical detection assays. This method is thus an improvement over the preferred two-step procedure described in application Ser. No. 264,131.

The buffered methanol solution used for the optimum extraction of the drug metabolites from the meconium has a pH between about 6 and 7. A buffer, such as 0.1M phosphate buffer, is used to maintain the pH. The preferred buffer is a mixture of sodium or potassium monophosphate and biphosphate.

The buffered methanol extract is further cleared of particulate matter by centrifugation using micropartition centrifuge tubes.

Once the drug metabolites are extracted from the meconium and filtered, standard assays are performed in order to detect the presence of the drug metabolites. These assays can be radioimmunoassays, enzyme immunoassay (ELISA or EMIT) using antibodies or appropriate probes which are specific for the drug metabolites. The antibody or multiple antibody sandwich assays is well known to those skilled in the art. Fluorescent polarization (TDX) assays and gas chromatography/mass spectroscopy can also be used to identify the metabolites. Further still, other quantitative or qualitative chemical tests can be used to assay for the drug metabolites in the isolated solution as is well known to those skilled in the art.

SPECIFIC DESCRIPTION

Methods

Meconium was collected from infants some of whom were born to mothers who by history had abused drugs during pregnancy, commonly heroin, cocaine, methadone, cannabinoids, amphetamines, barbiturates and benzodiazepines. The stools were obtained directly from the diaper.

Results

EXAMPLE 1

The method of this Example involves a one-step drug extraction using buffered methanol and analysis by enzyme immunoassay (EMIT) or fluorescent polarization method (TDX) or radioimmunoassay The steps in the method are:

1. Measure 0.2 to 0.5 g of meconium and suspend in 2 to 5 ml of 0.1 M phosphate buffered methanol (4:1 v/v aqueous buffered solution to methanol, pH = 6.4 to 6.8).
2. Centrifuge at 2000 rpm for 10 minutes
3. Transfer supernate to Amicon Centrifree ™ (American Division, W. R. Grace and Co., Danvers, MA) micropartition tubes and centrifuge at 2100 rpm for 30 minutes.
4. Obtain aliquots of the filtrate and analyze in duplicate for cocaine, opiates, cannabinoids and/or methamphetamine by enzyme immunoassay (EMIT - Sylva Co., Palo Alto, CA) or fluorescent polarization method (TDX, Abbott Laboratories Diagnostics Div., Irving, TX)

The minimum concentration values for testing found using these methods were: cannabinoid 50 ng/ml; cocaine 50 ng/ml; opiate 60 ng/ml; methamphetamine 50 ng/ml, which are acceptable for most purposes.

The accuracy of the modified method was tested by comparing the results of simultaneous analysis of 61 meconium samples for cocaine, opiate and cannabinoid metabolites by the original method (described in the Examples of U.S. Pat. application Ser. No. 264,131) using a radioimmunoassay and the improved method is shown in Tables I–III).

TABLE I

Comparison of Morphine Detection by the Original and Modified Methods[1]:

| Modified Method | Original Method | | Total |
|---|---|---|---|
| | Negative | Positive | |
| Negative | 52 | 0 | 52 |
| Positive | 1 | 8 | 9 |
| Total | 53 | 8 | 61 |

Sensitivity = 8/8 (100%)
Specificity = 52/53 (98%)
+ Predictive value 8/9 = 89%
− Predictive value 52/52 = 100%
[1]The original method is treated as the "gold" standard by which the improved method is judged.

TABLE II

Comparison of Cocaine Detection by the Original and Modified Methods:

| Modified Method | Original Method | | Total |
|---|---|---|---|
| | Negative | Positive | |
| Negative | 21 | 1 | 22 |
| Positive | 1 | 38 | 39 |
| Total | 22 | 39 | 61 |

Sensitivity = 38/39 (98%)
Specificity = 21/22 (95%)
+ Predictive value 38/39 (97%)
− Predictive value 21/22 = (95%)

TABLE III

Comparison of Cannabinoid Detection by the Original and Modified Methods:

| Modified Method | Original Method | | Total |
|---|---|---|---|
| | Negative | Positive | |
| Negative | 39 | 1 | 40 |
| Positive | 0 | 0 | 0 |
| Total | 39 | 1 | 40 |

In the 61 samples analyzed, opiates were detected in 8 (13%) by the original method and in 9 (15%) by the modified method; cocaine was detected in 39 (64%) by the original method and in 39 (64%) by the modified method. The sensitivity and specificity of the modified method for opiate detection was 100% and 98%, respectively (positive and negative predictive values of 89% and 100%, respectively); for detecting cocaine, sensitivity and specificity of 98% and 95%, respectively (positive and negative predictive values of 97% and 95%, respectively. Forty samples were available for analysis for cannabinoids; 40 were found to be negative by the modified method; 39 were negative and 1 positive by the original method.

It was concluded that the improved method for meconium testing was useful for mass drug screening in the newborn infant. The method is easy, rapid and highly sensitive and specific for the drugs analyzed. Likewise, adaptation of the test to enzyme immunoassay (rather than radioimmunoassay) makes it practical for clinical laboratory use.

EXAMPLE 2

Until recently, various immunoassays have been the only analytical method used to analyze meconium for drugs. GC/MS (GC/mass spectroscopy) was adapted to meconium testing. This provides for the definitive identification of drugs in meconium, as well as precise information on the types of drug metabolite present. This Example 2 shows GC/MS analysis of meconium for cocaine.

The steps of the method are:

1. Obtain 0.5 to 1.0 g of meconium and suspend in 5 to 10 ml of 0.1 M Phosphate buffered methanol (4:1 v/v aqueous buffered solution to methanol, pH = 6.4 to 6.8).
2. Centrifuge at 2000 rpm for 10 minutes.
3. Transfer supernate to Amicon Centrifree ™ micropartition tubes and centrifuge at 2100 rpm for 30 minutes.
4. Recover filtrate and subject to solid phase extraction using a Bond-Elute column (Analytichem Intl., Harbor City, CA) utilizing the protocol for cocaine.
5. Treat the purified residue with BSTFA (N,O-bis-trimethylsilyl-trifluoracetamide) to form the trimethylsilyl derivatives and inject into a Finnigan ITD BC/MS (Finnigan Corp., San Jose, CA).
6. Cocaine and benzoylecgonine mass spectra are identified through their characteristic ion masses (cocaine - m/z 82, 105, 182, 303; benzoylecgonine = m/z 82, 105, 240, 361.

RESULTS: Eight meconium samples, all positive for cocaine by enzyme (EMIT) and radioimmunoassays per the method described in the Examples of U.S. Pat. application Ser. No. 264,131 (at cutoff concentration of 50 ng/ml) were analyzed by GC/MS according to the above method. Cocaine or its metabolites, benzoylecgonine were detected in the samples analyzed by GC/MS: 6/9 (65%) showed the parent compound, cocaine and 7/9 (78%) showed benzoylecgonine (Table IV).

TABLE IV

Distribution of cocaine and benzoylecgonine GC/MS Results for Meconium

| Sample # | BE | Cocaine |
|---|---|---|
| 1 | + | + |
| 2 | + | − |
| 3 | + | + |
| 4 | + | + |
| 5 | + | + |
| 6 | + | − |
| 7 | − | + |
| 8 | + | − |
| 9 | − | + |
| Total | 7/9 (78%) | 6/9 (67%) |

It will be appreciated that the foregoing description is only illustrative of the present invention and that this invention is limited only by the hereinafter appended claims.

I claim:

1. A method for detecting maternally transferred drug metabolites in a newborn infant which comprises:
   (a) isolating meconium from the newborn infant
   (b) extracting any drug metabolites present from the meconium in an aqueous solution containing methanol in an amount of less than about 30% by volume with a buffered pH between about 6 and 7; and
   (c) assaying the solution for the drug metabolites.

2. The method of claim 1 wherein after the extraction step solids present in the meconium are removed by centrifugation from the solution.

3. The method of claim 1 wherein the solution is buffered with a phosphate to a pH between about 6 and 7.

4. The method of claim 3 wherein the phosphate is 0.1M.

5. The method of claim 1 wherein the drug metabolites are selected from the group consisting of cocaine, morphine, cannabinoids and methamphetamine metabolites.

6. The method of claim 1 wherein the infant is human and the meconium is fecal.

7. The method of claim 1 wherein the infant is treated for the drug metabolites which are detected.

8. The method of claim 7 wherein the infant is human.

9. The method of claim 1 wherein the assay is an immunoassay.

10. The method of claim 9 wherein the assay is an enzyme linked immunoassay.

11. The method of claim 9 wherein the assay is a radioimmunoassay.

12. The method of claim 1 wherein the assay is by fluorescent polarization.

13. The method of claim 1 wherein the assay is by gas chromatography.

14. The method of claim 13 wherein in addition as a control the solution is assayed by mass spectroscopy which identifies peaks uniquely produced by the drug metabolites.

15. The method of claim 14 wherein prior to assaying, the metabolites in the solution are reacted with N,O-bis-trimethylsilyl-trifluoroacetamide to form trimethyl silyl derivatives of the metabolites.

16. The method of claim 1 wherein in addition as a control the solution is assayed by mass spectroscopy which identifies peaks uniquely produced by the drug metabolites.

17. The method of claim 16 wherein prior to assaying, the metabolites in the solution are reacted with N,O-bis-trimethylsilyl-trifluoroacetamide to form trimethyl silyl derivatives of the metabolites.

18. The method of claim 1 wherein the drug metabolites are selected from the group consisting of cocaine, morphine, cannabinoid and amphetamine metabolites.

* * * * *